(12) United States Patent  (10) Patent No.: US 7,619,098 B2
Peschel et al.  (45) Date of Patent: Nov. 17, 2009

(54) METHOD FOR PRODUCING PHTHALIC ANHYDRIDE THAT CONFORMS TO SPECIFICATIONS

(75) Inventors: Werner Peschel, Freinsheim (DE); Matthias Kummer, Weisenheim (DE); Marcus Bechtel, Dossenheim (DE)

(73) Assignee: BASF Aktiengesellschaft (DE)

( * ) Notice: Subject to any disclaimer, the term of this patent is extended or adjusted under 35 U.S.C. 154(b) by 0 days.

(21) Appl. No.: 11/813,181

(22) PCT Filed: Dec. 31, 2005

(86) PCT No.: PCT/EP2005/014159

§ 371 (c)(1), (2), (4) Date: Jun. 29, 2007

(87) PCT Pub. No.: WO2006/072463

PCT Pub. Date: Jul. 13, 2006

(65) Prior Publication Data

US 2008/0207925 A1  Aug. 28, 2008

(30) Foreign Application Priority Data

Jan. 7, 2005 (DE) .................... 10 2005 000 957

(51) Int. Cl.
*C07D 307/89* (2006.01)
(52) U.S. Cl. .................... 549/250; 203/86; 203/89; 203/91
(58) Field of Classification Search ............... 549/250; 203/89, 91, 86
See application file for complete search history.

(56) References Cited

U.S. PATENT DOCUMENTS

| 3,699,008 | A | 10/1972 | Brendt et al. |
| 4,008,255 | A | 2/1977 | Wirth et al. |
| 4,547,578 | A | 10/1985 | Gude et al. |
| 6,570,026 | B1 | 5/2003 | Peschel et al. |
| 2004/0060809 | A1 | 4/2004 | Disteldorf et al. |

FOREIGN PATENT DOCUMENTS

EP  1233012 A1  8/2002

(Continued)

OTHER PUBLICATIONS

Durst et al , Experimental Organic Chemistry, 1980, McGraw-Hill, Inc. p. 49. (3 pages).*

(Continued)

*Primary Examiner*—Taylor Victor Oh
(74) *Attorney, Agent, or Firm*—Connolly Bove Lodge & Hutz

(57) ABSTRACT

Process for the preparation of on-spec phthalic anhydride by the distillative purification of crude phthalic anhydride at reduced pressure, where the crude phthalic anhydride is passed to the distillation column above a side take-off, the low-boiling components are removed at the top of the column or in the vicinity of the top of the column and the on-spec phthalic anhydride is removed from the side take-off of the column, in which a distillation column is used whose number of theoretical plates located above the supply of the crude phthalic anhydride into the distillation column is 10 to 20 and the column is operated at a reflux ratio of from 0.1 to 0.5.

11 Claims, 1 Drawing Sheet

FOREIGN PATENT DOCUMENTS

WO    WO-01/14308 A1    3/2001

OTHER PUBLICATIONS

Suter, H., "Phthalicanydride and its use", Steinkopff Verlag, 1972, pp. 39-46.

Ullmanns Encyclopedia of Industrial of Chemical Technology, 5th Edition, 1992, vol. A20, pp. 181-189.

Kirk-Othmer Encyclopedia of Chemical Technology, 4th Edition, vol. 18, pp. 997-1006, 1996.

"Phtalsäureanhydrid", Europa-Chemie, 1695, Issue 21, p. 7, 1965.

Organics, 1975, 14th Edition, pp. 42-44, 50-60.

Vauck, W. R. A. et al., "Basic Operations of Chemical Process Technology", 2000, Chapter 10.4.2, pp. 710-761.

Kirk-Othmer, Encyclopedia of Chemical Technology, 4th Edition, 1993, vol. 8, pp. 311-358.

* cited by examiner

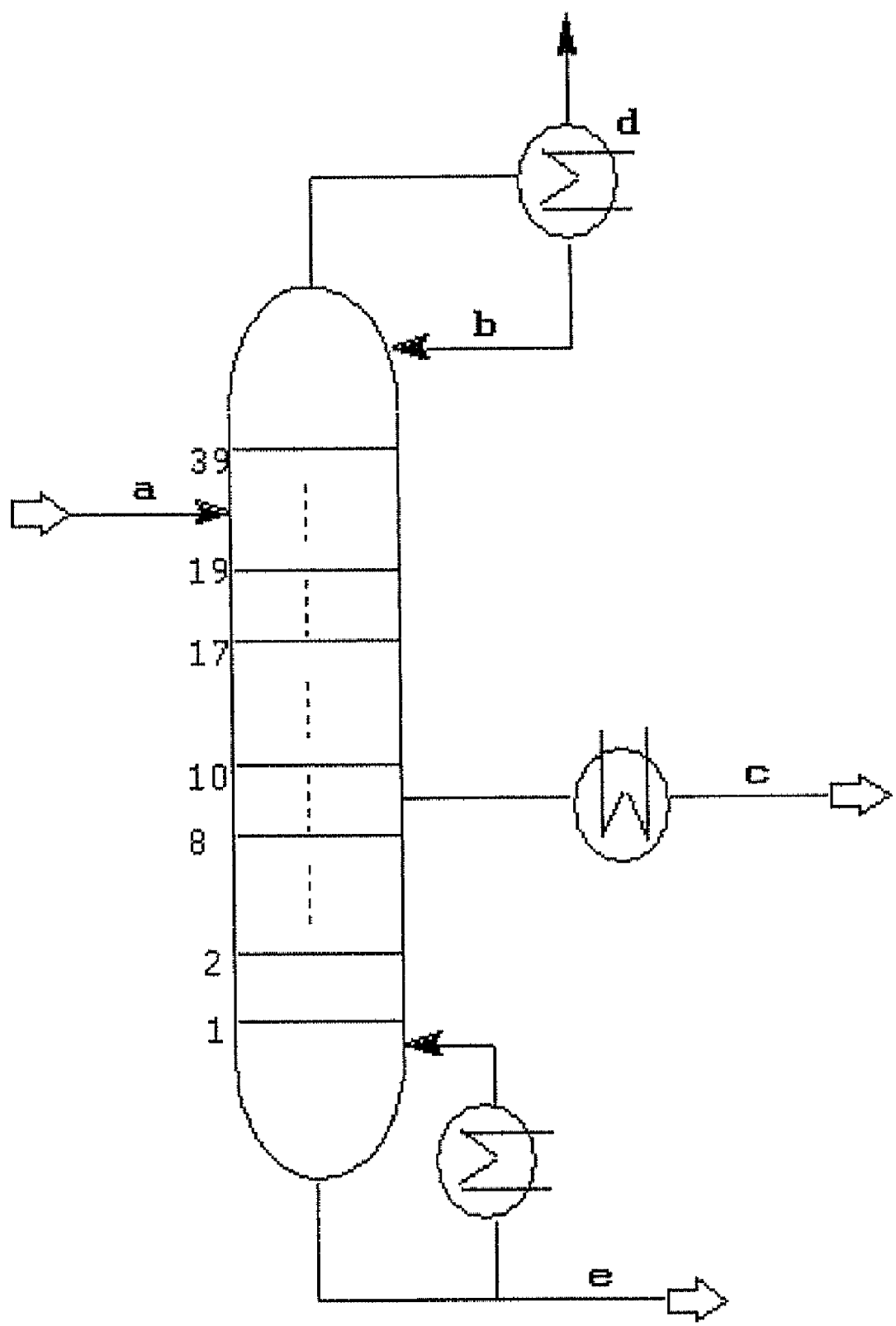

METHOD FOR PRODUCING PHTHALIC ANHYDRIDE THAT CONFORMS TO SPECIFICATIONS

RELATED APPLICATIONS

This application is a national stage application (under 35 U.S.C. 371) of PCT/EP2005/014159 filed Dec. 31, 2005, which claims benefit of German application 10 2005 000 957.3 filed Jan. 7, 2005.

DESCRIPTION

The present invention relates to a process for the preparation of on-spec phthalic anhydride by the distillative purification of crude phthalic anhydride, where the crude phthalic anhydride is passed to the distillation column above a side take-off, the low-boiling components are removed at the top of the column or in the vicinity of the top of the column and the on-spec phthalic anhydride is removed from the side take-off of the column.

Phthalic anhydride (also called "PA" below) is an important basic chemical in the chemical industry. It is used to a considerable extent as a starting material for dialkyl phthalates, which are used in large amounts as plasticizers for plastics such as PVC. Crude PA is prepared industrially from naphthalene and/or o-xylene by catalytic oxidation in the gas phase. For the abovementioned purposes, preference is given to using a PA which has been prepared from o-xylene. The discharges of said customary preparation processes have, based on their total weight, usually more than 99% by weight of PA. This crude PA is isolated in most cases in liquid form or as a solid using separators.

Depending on the chosen preparation process and particularly on the starting materials and the catalysts, the product comprises a spectrum, specific in each case, of impurities and by-products (cf. e.g.: H. Suter: "Phthalsäureanhydrid und seine Verwendung" [Phthalic anhydride and its use], Dr. Dietrich Steinkopff Verlag, Darmstadt, 1972, page 39 ff.; shortened below to "Suter").

On the market, a PA grade with the following specification limits is expected:

| Solidification point (° C.) | min. 130.8 |
| --- | --- |
| Mass fractions (% by weight): | |
| PA | min. 99.8 |
| MA | max. 0.05 |
| Benzoic acid | max. 0.10 or |
| | max. 0.002 for fragrance quality |
| Phthalic acid | max. 0.1 |
| Melt color number (Hazen) | max. 20 |
| Heat color number (Hazen) | max. 40 |

In the art, over the period during which phthalic anhydride has been prepared on an industrial scale it has become established practice to separate off the by-products by distillation (cf. e.g.: "Ullmann's Encyclopedia of Industrial Chemistry", 5th Edition, Vol. A20, VCH Verlagsgesellschaft mbH, Weinheim, 1992, pages 181 to 189; shortened below to "Ullmann"; Kirk-Othmer "Encyclopedia of Chemical Technology", 4th Edition, Vol. 18, John Wiley & Sons, New York, 1996, pages 997 to 1006, shortened below to Kirk-Othmer"). However, impurities which are low-boiling and/or distill azeotropically, some of which have an intense intrinsic color, cause great problems for the person skilled in the art, despite being present in comparatively small amounts.

The distillation—especially its continuous operation frequently of particular interest for reasons of cost—is usually carried out by means of two columns in order to obtain a sufficiently pure PA. In the first step, the low-boiling components (for example the greater parts of benzoic acid, maleic anhydride, citraconic anhydride), i.e. substances with a boiling point below the boiling point of PA, are generally separated off; in a second step, PA is then distilled off from the high-boiling components (for example phthalic acid, certain color-imparting components, condensation products of ingredients of crude PA), i.e. substances with higher boiling points than that of PA or of undistillable constituents.

Other processes for purifying crude phthalic anhydride comprise its thermal and, if appropriate, additional chemical treatment before its distillation, for example the process as in U.S. Pat. No. 4,547,578, or the absorption of gaseous PA in paraffin oil, crystallization of the PA and subsequent distillative purification of the remelted PA crystals as in U.S. Pat. No. 4,008,255. All of these processes require high expenditure on apparatus, have a high energy consumption and are consequently uneconomical.

In "Suter" (loc. cit., page 45) reference is made to a single-stage continuous distillation of PA (Ruhröl, Europa—Chemie Volume 21, p. 7 (1965)), but no details are given.

Particularly high requirements are placed on those esters of phthalic acid synthesized from PA which are to be used as solvents or extenders in perfumes or cosmetics. However, the presence of small amounts of maleic acid, citraconic acid and anhydrides thereof and especially of benzoic acid in the PA leads to esterification products of these substances, which have intense, characteristic odor notes, for example a diffuse fruity note in the case of ethyl benzoate. Such impurities are usually to be removed following the ester synthesis by means of a combined washing and extraction step. This process is very complex and normally does not make the preceding, customary distillation of the crude PA dispensible.

Attempts to solve the problem of separating off the impurities, which are only present in small amounts in the crude PA but have a very disruptive effect depending on the intended use of the PA, to correspond to the specifications required by customers are made according to WO 01/14308 by means of a single-stage distillative process. In this process, on-spec PA is obtained by distillative purification of crude PA by passing crude PA to a distillation column which is operated at reduced pressure, removing the low-boiling components at the top or in the vicinity of the top of the distillation column and removing the on-spec PA from the column via a side take-off.

At a theoretical number of plates of in total approximately 18, according to example of WO 01/14308, at a reflux ratio of 0.6, a phthalic anhydride with a benzoic acid content of 30 ppm by weight is obtained. For fragrance applications in particular, a further distillative reduction of the benzoic acid content in the PA is desired. Moreover, in this process a large amount of energy is consumed due to the high reflux ratio.

However, the further distillative reduction of the benzoic acid content is difficult. Although it appears possible, by reducing the reflux ratio, to draw off more benzoic acid via the top of the column, this measure, however, leads to an increased discharge of PA via the top of the column together with the low-boiling components and consequently to considerable PA losses. This effect is evident from EP-A 1 233 012, which likewise has a single-stage process for the distillation of PA as subject-matter. In the only example of EP-A 1 233 012, at a feed to the column of 1000 g/h of phthalic anhydride and a reflux of 530 g/h, corresponding to a reflux ratio of 0.53, although a phthalic anhydride is obtained whose benzoic acid content is only 15 ppm by weight, the recovery rate for the phthalic anhydride drops to only 97%, which renders the process uneconomical.

The present invention was therefore based on the object of providing an improved process for the distillative production of on-spec PA compared with the prior art. In particular, the process was to be able to produce on-spec PA with a low content of benzoic acid and other low-boiling components without impairing the color number of the PA with low energy consumption and small PA losses.

BRIEF DESCRIPTION OF THE DRAWINGS

The single FIGURE schematically illustrates an arrangement for practicing the process of this invention.

DETAILED DESCRIPTION

Accordingly, a process for the preparation of on-spec phthalic anhydride by the distillative purification of crude phthalic anhydride at reduced pressure, where the crude phthalic anhydride is passed to the distillation column above a side take-off, the low-boiling components are removed at the top of the column or in the vicinity of the top of the column and the on-spec phthalic anhydride is removed from the side take-off of the column, has been found, wherein a distillation column is used whose number of theoretical plates located above the supply of the crude phthalic anhydride to the distillation column is 10 to 20 and the column is operated at a reflux ratio of from 0.1 to 0.5.

According to the invention, the distillation column used in the process according to the invention is operated at a reflux ratio of from 0.1 to 0.51 preferably from 0.2 to 0.45 and particularly preferably from 0.25 to 0.45. Reflux ratio ("RR") is the term used to refer to the quotient $$RR = \frac{\text{Amount of reflux/Time unit}}{\text{Feed to the column/Time unit}}. \quad (1)$$

The distillation column to be used according to the invention is designed according to the invention such that the number of theoretical plates located above the supply of the crude PA into the column is 10 to 20, preferably 10 to 15.

Theoretical plate, in the literature often also referred to as "theoretical tray", is defined as being the column unit which brings about an enrichment of readily volatile component corresponding to the thermodynamic equilibrium between liquid and vapor in a single distillation process according to equation (2)

$$\frac{Y_1}{1-Y_1} = \alpha \frac{X_1}{1-X_1}. \quad (2)$$

In this equation, $X_1$ is the mole fraction of the readily boiling component in the liquid phase, $Y_1$ is the mole fraction of the readily boiling component in the vapor space and the constant $\alpha$ is the relative volatility given by the quotient of the vapor pressure P of the pure components A and B of the mixture to be distilled $$\frac{P_A}{P_B} = \alpha. \quad (3)$$

If the difference between $P_A$ and $P_B$ is small, complete separation of the components in a single distillation operation, i.e. in one theoretical plate, can consequently not be achieved. In order to achieve complete separation of the two components, the individual distillation operation has to be repeated—generally many times—in which case the term used is then rectification when summarizing these many individual distillation operations in one column. Each of the "practical" trays installed in such a distillation column, which may be configured in different shapes, represents as it were by itself a new distillation pot. In general, these "practical" trays do not achieve the effect of a theoretical plate (i.e. of a theoretical tray). Accordingly, the separation efficiency of a distillation column is usually given by the number n of theoretical plates present therein. The number n of theoretical plates present in a column or, if referring to one section of the column, in this section of the column can be calculated from equation (4)

$$\frac{Y_n}{1-Y_n} = \alpha^n \frac{X_1}{1-X_1} \quad (4)$$

in which $Y_n$ represents the mole fraction of the readily boiling component in the vapor space after repetition n times of the evaporation-condensation operation, divided by its resolution based on n.

It is clear that the above explanations with regard to the definition of a theoretical plate in this form only apply to a two-component system with ideal or virtually ideal behavior. Although the PA to be purified according to the invention comprises a large number of different impurities, the statement according to the invention of the number of theoretical plates located above the crude PA feed into the column refers merely to the system of the two components benzoic acid and phthalic anhydride to be separated.

The above statements relating to the meaning of the term theoretical plate serve merely to explain and to clarify this term within the meaning of the present invention and are familiar to the person skilled in the art e.g. from textbooks, such as Organikum [Organics] (14th Edition, pp. 42-44 and pp. 50-60, VEB Deutscher Verlag der Wissenschaften, Berlin 1975) or Vauck; Müller, Grundoperationen chemischer Verfahrenstechnik [Basic operations of chemical process technology] (11th Edition; Chapter 10.4.2 Gegenstromdestillation [Countercurrent distillation], pp. 710-761; Deutscher Verlag für Grundstoffindustrie, Stuttgart 2000), or from compilations, as in Kirk-Othmer, Encyclopedia of Chemical Technology (4th Ed., Vol. 8, Chapter: Distillation, pp. 311-358, John Wiley & Sons, New York 1993), which also comprise even more detailed and more far-reaching information on carrying out distillations.

The total number of theoretical plates of the distillation columns which can be used in the process according to the invention is generally 15 to 40, preferably 20 to 30 and particularly preferably 22 to 26 theoretical plates.

While it is critical to observe the number according to the invention of the plates located above the feed of the crude PA into the column to achieve the object on which the invention is based, there are certain variation possibilities for the layout of the number of theoretical plates in the two sections of the column positioned below the feed of the crude PA, namely the section between feed of crude PA into the column and the side take-off and the section of the column below the side take-off. In general, the section below the feed of crude PA to the side take-off is designed such that it has a number of theoretical plates of in general from 3 to 15, preferably from 6 to 12. The section of the distillation column below the side take-off is generally designed such that it has a number of theoretical plates of in general from 2 to 8, preferably from 3 to 6.

To carry out the process according to the invention it is possible to use distillation columns customary per se, for example tray columns, columns containing dumped packings and columns containing stacked packings or columns in which there is a combination of the features of the column types specified above. According to the type of column used, it can be equipped with internals customary per se, such as trays, dumped packings or stacked packings, for example with bubble trays, tunnel trays, valve trays, sieve trays, dual-flow trays and/or lattice trays, with Pall Rings®, Bern® saddles, wire mesh rings, Raschig Rings®, Intalox® saddles, Interpak® dumped packings and Intos®, but also stacked packings, such as, for example, Sulzer-Mellapak®, Sulzer-Optiflow®, Kühni-Rombopak® and Montz-Pak®, and fabric packings. In the region below the column feed, internals which are also suitable for solids, in particular dual-flow trays, are preferably chosen. Trays and dumped packings of the abovementioned designs are generally suitable for this purpose.

The number of theoretical plates above the crude PA feed into the distillation column for achieving the number to be adjusted according to the invention, and the number of practical trays required to establish the desired number of theoretical plates in the two sections of the column positioned below the supply of crude PA into the distillation column and consequently also the height of the column is calculated to correspond to the separation efficiency of the column internals used. By contrast, the basis used for configuring the diameter of the distillation column is the throughput desired with the column or, in other words, its desired production capacity. Knowing the configuration criteria according to the invention for the distillation column to be used according to the invention it is possible to carry out the calculations required for this in accordance with the chemical engineering calculation methods familiar to the person skilled in the art.

To produce the reflux on the distillation column, the low-boiling component fraction drawn off in gaseous form at the top or in the vicinity of the top of the column is condensed in a condenser and the condensate is returned to the column corresponding to the desired reflux ratio again to the top of the column or in the vicinity of the top of the column.

The distillation column can be operated with standard commercial evaporators. Liquid-phase evaporators can be used expediently, in which case these are advantageously designed as falling-film evaporators. The use of falling-film evaporators permits a gentle evaporation of the bottom liquid due to the short average residence time of the bottom liquid in the evaporator, as a result of which the tendency toward solid formation and also to the formation of decomposition products during evaporation is reduced and thus the pure PA yield and also the cost-effectiveness of the process is improved.

The high-boiling components can be removed continuously or discontinuously from the bottom of the distillation column or the liquid evaporation residue in the evaporator and be disposed of.

The column can generally be operated at an absolute pressure at the top of the column of from 0.05 to 0.5 bar, preferably 0.1 to 0.3 bar, particularly preferably at 0.12 to 0.20 bar.

The temperatures in the column are at the top of the column generally 160 to 220° C., preferably 170 to 200° C. and especially 175 to 185° C., and at the bottom of the column 220 to 260° C., preferably 225 to 250° C. and especially 230 to 245° C. The temperature at the side take-off is generally 210 to 250° C. and preferably 220 to 240° C.

The distillation can be carried out discontinuously or preferably continuously. The crude PA can be passed to the column via the feed in gaseous form or preferably in liquid form. The purified on-spec PA can be removed in gaseous form from the side take-off of the distillation column, which is situated below the feed of the crude PA into the distillation column.

In a preferred embodiment of the process according to the invention where tray columns are used, drop separators can be installed at the side take-off for the gaseous pure PA inside or outside of the distillation column.

Using the process according to the invention it is possible to obtain a PA with a content of benzoic acid of less than 20 ppm, preferably between 5 and less than 20 ppm. The process according to the invention is very particularly suitable for a crude PA which has a content of PA of from 95.0 to 99.8% by weight and a content of benzoic acid of from 0.1 to 5.0% by weight and especially from 0.2 to 1.0% by weight.

The process according to the invention is particularly suitable for crude PA as obtained by catalytic gas-phase oxidation of o-xylene and containing preferably more than 95% by weight and in particular more than 98% by weight of PA.

With the process according to the invention, a melt color number of the PA of less than 10 APHA and a heat color number of less than 20 APHA is achieved.

The on-spec PA is usually cooled directly after being removed from the column and obtained in the form of a liquid or, following solidification, in the form of a solid. An even higher degree of purity can be attained, if desired, by finely distilling the PA for example over a side column, or by mounting a dividing wall axially above a certain region in the column (so-called Petlyuk arrangement). Recrystallization is also suitable here.

The recovery rate of PA at the side take-off based on the content of PA in the feed to the column is generally 98% and higher.

The purity of the resulting PA can be determined by generally known analytical methods, such as gas chromatography, UV spectroscopy and acid-base titration. Since a PA without coloring impurities is required for most use purposes, particular importance is attached to characterization by the so-called color numbers—particularly the melt color number and the heat color number. Color changes in the PA under thermal stress are of practical importance since PA is normally stored and transported in the molten state—for example at 160° C. In particular, the melt color number (APHA/Hazen color scale, cf. W. Liekmeier, D. Thybusch: Charakterisierung der Farbe von klaren Flüssigkeiten [Characterization of the color of clear liquids], Editor: Bodenseewerk Perkin-Elmer GmbH, Überlingen, 1991) is generally ascertained by determining the color number of PA immediately after taking the sample at a temperature of 160° C. Furthermore, the heat color number is generally ascertained by keeping the PA at 250° C. for 90 minutes and then measuring the color number.

By applying the measures according to the invention the object on which the invention is based is solved very well. On account of the low reflux ratio, removal of the benzoic acid and other low-boiling components present in the crude PA apart from very low residual contents is possible with a significantly reduced energy consumption compared with the prior art. As a result of increasing the number of theoretical plates above the supply of crude PA into the distillation column, on the other hand, the losses of PA as a result of discharge with the low-boiling components are minimized. Contrary to expectations, these measures also do not lead to an increase in the color number in the pure PA discharged via the side take-off of the distillation column. This is surprising since the reflux stream running off at the side take-off into the bottom is, due to the low reflux ratio used, highly concentrated in color-imparting impurities, for which reason disadvantageous effects on the color number of the pure PA were expected. Besides a low content of low-boiling components, in particular benzoic acid, the maintenance of a low color number in the purified PA is particularly critical for the subsequent use of the PA since the color-imparting impurities darken over time, in particular upon thermal stress—the PA is usually transported and stored in the molten state—and/or in the presence of oxygen and lead to the yellowing or brown discoloration of the products prepared therewith, thus rendering them virtually unsaleable.

The invention is explained by reference to the following examples:

EXAMPLES

A) Apparatus Used

A tray column in accordance with schematic drawing 1 was used. The number of trays in the column could be varied. For carrying out the experiments, 32 to 39 valve trays, corresponding to a number of 22 to 27 theoretical plates, were installed depending on the examples. The column had a diameter of 50 mm. The side take-off (c) was located between the 10th and 11th tray above the bottom (roughly in the region between the seventh and eighth theoretical plate), the feed of the crude PA (a) was located between the 21st and 22nd plate above the bottom (roughly in the region of the fourteenth theoretical plate). In the drawing the 1st and 2nd trays are shown, while the other trays are indicated by vertical dashed lines.

B) Crude PA Used

The crude PA used for the distillation was one which had been prepared by gas-phase oxidation of o-xylene over a fixed bed in the presence of a catalyst consisting of a support core coated with the catalytically active metal oxides cesium oxide (calculated as 0.4% by weight of cesium), vanadium oxide (4% by weight) and titanium dioxide (95.6% by weight) (cf. WO-A 01/14308). The loading in the reactor was 86 g of o-xylene per $m^3$ (STP) of air. The reactor temperature was between 350 and 450° C.

The resulting crude PA had the following weight-based composition:

| | |
|---|---|
| 99.24% by weight | of PA |
| 0.2% by weight | of benzoic acid |
| 200 ppm | of maleic anhydride |
| 20 ppm | of citraconic anhydride |
| 0.5% by weight | of phthalic acid | and the remainder to 100% by weight of other substances.

C) Generally Applicable Process Steps

The melt color number was determined immediately after removing the sample from the distilled PA. The heat color number was determined as follows: a sample of PA was heat-treated in a drying oven for 1.5 hours at a temperature of 250° C. The color number was then measured.

Example 1

Comparative Example

Distillation According to the Prior Art (EP-A 1 233 012); Reference Numerals Refer to the FIGURE 1000 g of the crude PA according to section B) above were passed continuously to the column (a). Within this period, an amount of energy of 720 kJ/kg of crude PA was supplied to the column. At a reflux of 530 g (b), an absolute pressure of 0.17 bar at the top of the column, a temperature of 198° C. at the top of the column and 238° C. at the bottom of the column, 970 g of purified PA were removed within the same time via the side take-off at 221° C., condensed and isolated (c). The reflux ratio in the column was accordingly 0.53 and the yield of PA purified in this way was 97.8% by weight, based on the crude PA supplied to the column. The top take-off via (d) was condensed in a cold trap and was about 7 g; the bottom take-off via (e) was about 15 g and comprised the high-boiling components and nondistillable fractions. Analysis of the PA isolated via the side take-off at (c) gave the following weight-based composition:

| | |
|---|---|
| 99.97% by weight | of PA |
| 15 ppm | of benzoic acid |
| <10 ppm | of maleic anhydride |
| <10 ppm | of citraconic anhydride |
| 0.02% by weight | of phthalic acid | and the remainder to 100% by weight of other substances.

The melt color number was 5-10 APHA. The heat color number of the PA was 10-20 APHA.

Example 2

First Example According to the Invention 1150 g of the crude PA according to section B) above were passed continuously to the column per hour (a). Within this period, an amount of energy of 690 kJ/kg was supplied to the column. At a reflux of 510 g (b), an absolute pressure of 150 mbar at the top of the column, a temperature of 192° C. at the top of the column and 235° C. at the bottom of the column, 1130 g of purified PA were removed within the same time via the side take-off at 224° C., condensed and isolated (c). The reflux ratio in the column was accordingly 0.44 and the yield of PA purified in this way was 99.0% by weight, based on the crude PA supplied to the column. The top take-off via (d) was condensed in a cold trap and was about 5 g; the bottom take-off via (e) was about 15 g and comprised the high-boiling components and nondistillable fractions. Analysis of the PA isolated via the side take-off at (c) gave the following weight-based composition:

| | |
|---|---|
| 99.97% by weight | of PA |
| 13 ppm | of benzoic acid |
| <10 ppm | of maleic anhydride |
| <10 ppm | of citraconic anhydride |
| 0.02% by weight | of phthalic acid | and the remainder to 100% by weight of other substances.

The melt color number was 5-10 APHA. The heat color number was measured as 10-20 APHA.

Example 3

Second Example According to the Invention 850 g of the crude PA according to section B) above were passed continuously to the column per hour (a). Within this period, an amount of energy of 675 kJ/kg were supplied to the column. At a reflux of 330 g (b), an absolute pressure of 125 mbar at the top of the column, a temperature of 184° C. at the top of the column and 232° C. at the bottom of the column, 840 g of purified PA were removed within the same time via the side take-off at 220° C., condensed and isolated (c). The reflux ratio in the column was accordingly 0.39 and the yield of PA purified in this way was 99.6% by weight, based on the crude PA supplied to the column. The top take-off via (d) was condensed in a cool trap and was about 3 g; the bottom take-off via (e) was about 7 g and comprised the high-boiling components and nondistillable fractions. Analysis of the PA isolated via the side take-off at (c) gave the following weight-based composition:

| | |
|---|---|
| 99.97% by weight | of PA |
| <10 ppm | of benzoic acid |
| <10 ppm | of maleic anhydride |
| <10 ppm | of citraconic anhydride |
| 0.02% by weight | of phthalic acid | and the remainder to 100% by weight of other substances.

The melt color number was 5-10 APHA. The heat color number was measured as 10-20 APHA.

TABLE

Comparison of the results from examples 1 to 3

| No. | RR | E [kJ/kg] | BA [ppm] | CN [APHA] | HCN [APHA] | TP | L [%] |
|---|---|---|---|---|---|---|---|
| 1 (comparison) | 0.53 | 720 | 15 | 5-10 | 10-20 | 5 | 2.2 |
| 2 (invention) | 0.44 | 690 | 13 | 5-10 | 10-20 | 10 | 1.0 |
| 3 (invention) | 0.39 | 675 | <10 | 5-10 | 10-20 | 13 | 0.4 |

No. Example number
RR Reflux ratio:

$$RR = \frac{\text{Amount of reflux/Time unit}}{\text{Feed to the column/Time unit}} \quad (1)$$

E  Energy input into the column in kJ/kg of crude PA
BA Content of benzoic acid in the distilled PA [ppm]
CN Melt color number of the distilled PA in accordance with Hazen [APHA]
HCN Heat color number of the distilled PA in accordance with Hazen [APHA]
TP Number of theoretical plates above the crude PA supply (a)
L  PA loss based on the amount of PA supplied with the crude PA to the distillation column

We claim:

1. In a process for the preparation of on-spec phthalic anhydride which comprises distillative purification a crude phthalic anhydride at reduced pressure, where the crude phthalic anhydride is passed to the distillation column above a side take-off, the low-boiling components are removed at the top of the column or in the vicinity of the top of the column and the on-spec plithalic anhydride is removed from the side take-off of the column, the improvement being in a distillation column is used whose number of theoretical plates located above the supply of the crude phthalic anhydride into the distillation column is 10 to 20 and the column is operated at a reflux ratio of from 0.1 to 0.5 to produce the phthalic anhydride with a reduced content of low-boiling components without impairing the color number of the phthalic anhydride and with reduced energy consumption and with reduced phthalic anhydride losses.

2. The process according to claim 1, wherein the column is operated at a reflux ratio of from 0.2 to 0.45.

3. The process according to claim 1, wherein the column is operated at a reflux ratio of from 0.25 to 0.4.

4. The process according to claim 1, wherein a distillation column is used whose number of theoretical plates located above the supply of the crude phthalic anhydride into the distillation column is 10 to 15.

5. The process according to claim 3, wherein a distillation column is used whose number of theoretical plates located above the supply of the crude phthalic anhydride into the distillation column is 10 to 15.

6. The process according to claim 1, wherein the on-spec plithalic anhydride is removed from the side take-off of the distillation column in gaseous form.

7. The process according to claim 5, wherein the on-spec phthalic anhydride is removed from the side take-off of the distillation column in gaseous form.

8. The process according to claim 1, wherein the distillation column used is a tray column operated with a falling-film evaporator.

9. The process according to claim 7, wherein the distillation column used is a tray column operated with a falling-film evaporator.

10. The process according to claim 1, wherein the distillation column used is a tray column on which drop separators are installed at the side take-off inside or outside of the column.

11. The process according to claim 9, wherein the distillation column used is a tray column on which drop separators are installed at the side take-off inside or outside of the column.

* * * * *